United States Patent [19]

White et al.

[11] Patent Number: 4,476,604

[45] Date of Patent: Oct. 16, 1984

[54] PRESSURE SENSING DEVICE FOR HOLDING A TOOTHBRUSH

[75] Inventors: Larry W. White, 111 W. Clinton, Hobbs, N. Mex. 88240; Luis Ingels, Azusa, Calif.

[73] Assignee: Larry W. White, Hobbs, N. Mex.

[21] Appl. No.: 498,840

[22] Filed: May 27, 1983

[51] Int. Cl.³ .............................................. A47B 9/04
[52] U.S. Cl. .................................. 15/105; 15/167 R; 434/263; 128/774
[58] Field of Search .................... 15/22 R, 22 C, 105, 15/167 R; 434/263; 433/72; 128/62 A, 774, 776, 777; 33/174 D; 340/665, 686; 116/202, 212

[56] References Cited

U.S. PATENT DOCUMENTS

| | | | |
|---|---|---|---|
| 2,875,458 | 3/1959 | Tsuda | 15/22 R |
| 2,877,477 | 3/1959 | Levin | 15/105 |
| 4,123,845 | 11/1978 | Fattaleh | |
| 4,253,212 | 3/1981 | Fujita | 15/167 R |
| 4,340,069 | 7/1969 | Yeaple | |

FOREIGN PATENT DOCUMENTS 2097663 11/1982 United Kingdom ............. 15/22 R

OTHER PUBLICATIONS

Fraleigh, McElhaney and Heisser, "Toothbrushing Force Study," *Journal of Dent. Res.*, Jan. Feb. 1967, vol. 46, pp. 209–214.

Breitenmoser, Mormann and Muhlemann, "Damaging Effects Of Toothbrush Bristle End Form on Gingiva," pp. 212–216.

Allen and Nahodil, "A Transducer For Measuring The Force Exerted On Teeth By A Toothbrush During Brushing," *J. Dent. Res.* Supplement to No. 5, p. 1272.

White, *Toothbrush Pressures Of Orthodontic Patients,* American Journal Of Orthodontics (Feb. 1983).

*Primary Examiner*—Peter Feldman
*Attorney, Agent, or Firm*—Banner, Birch, McKie & Beckett

[57] ABSTRACT

A device for sensing the amount of force applied to the teeth during brushing is disclosed. The device includes a toothbrush holder pivotally supported inside a sleeve. O-rings mounted on the holder act both as fulcrum for the holder and as resistance members to resist the pivoting of the holder inside the sleeve. An adjustment cap is threadedly mounted on the sleeve and can adjustably compress the O-rings to provide variable resistance to the pivoting of the holder. An electrical circuit comprised of fixed and floating contacts detects the holder pivotal movement and lights up a bulb to indicate that the holder is pivoting. A battery is carried in the sleeve to power the circuit.

20 Claims, 3 Drawing Figures

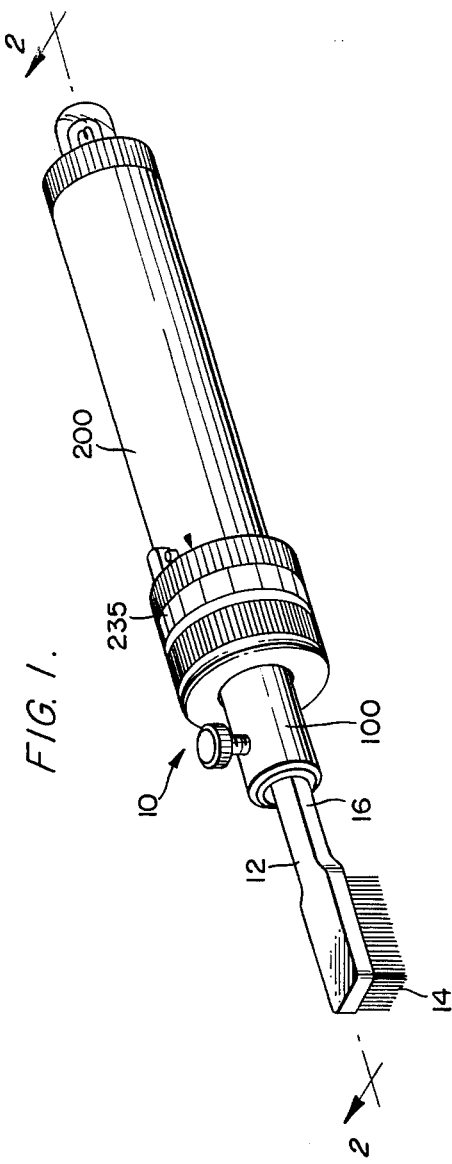
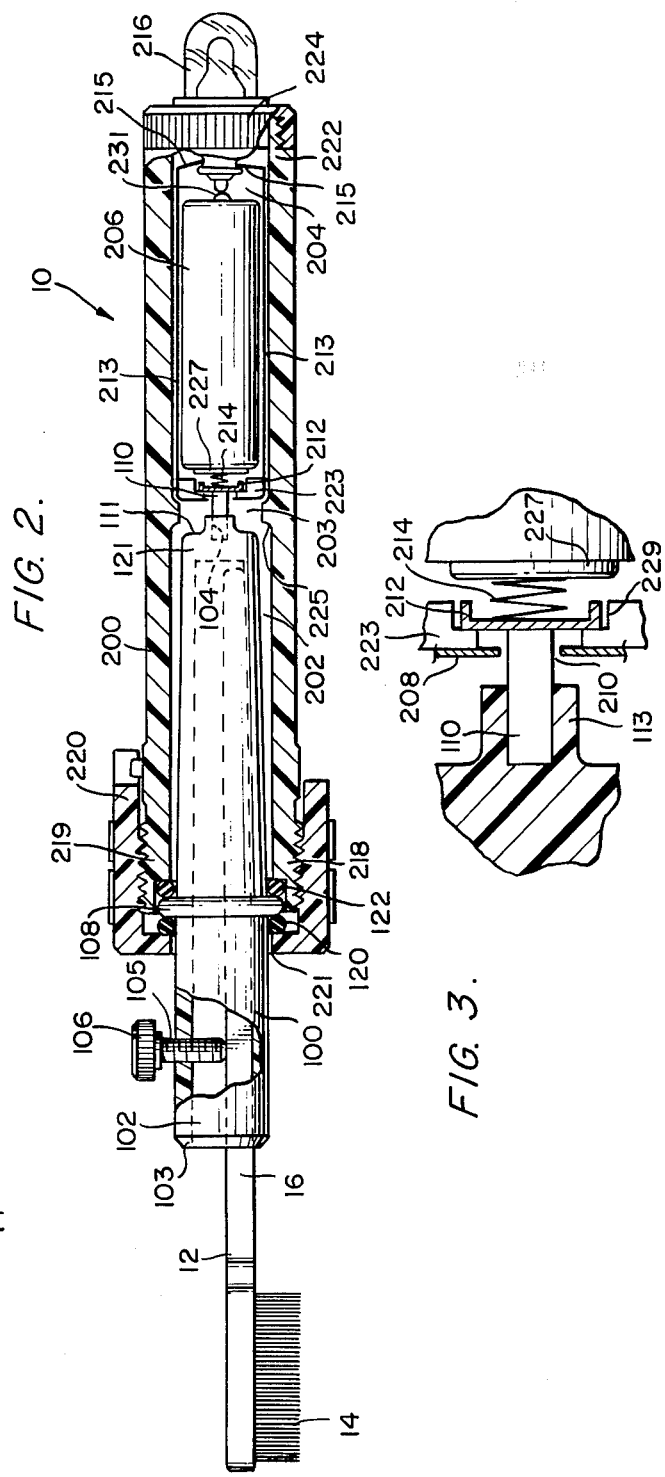

PRESSURE SENSING DEVICE FOR HOLDING A TOOTHBRUSH

TECHNICAL FIELD

The present invention relates to dental instructional devices. More particularly, the invention relates to a toothbrush holding device which indicates to the user that a preselected, but variable, amount of force is being applied to the teeth. The toothbrush holding device can be used as an instructional tool for guiding or teaching a user to gradually increase the amount of pressure applied during brushing.

BACKGROUND OF THE INVENTION

It has been demonstrated that effective toothbrushers exert a large amount of force against their teeth. On the other hand, ineffective toothbrushers exert far less force when they brush. In the past, poor toothbrushing habits often were attributed to poor brusher attitude; poor brushers commonly were assumed to be apathetic about their brushing habits. Howver, it is the belief of the applicant that many times poor toothbrushing results are caused by the application of inadequate force by the user against the teeth. Indeed, if the amount of force is corrected by instruction, the brusher will vastly improve the results of brushing.

Of necessity, instruction regarding the proper amount of force to apply during brushing must include a means for indicating to the user that a sufficient amount of force is in fact being applied to the teeth. An attempt at such an indicating means was made in Fugita U.S. Pat. No. 4,253,212, in which a force sensing device was located in the stem of a specially adapted toothbrush. The pressure sensing device was elastic, and when the stem bent under the force being applied to the teeth, the device detected the bending. An indicating device informed the brusher that an adequate amount of force was being used against the teeth.

Unfortunately, the Fugita device has two drawbacks. First, the stem must be custom made to include the sensing device. Thus, ordinary toothbrushes cannot be used with the Fugita device, increasing the expense and incovenience to the user. Second, the amount of pressure detected is not adjustable. As a result, the user cannot learn by gradually increasing the amount of force applied by a single toothbrush; rather he will be forced to apply the maximum preset amount of force to get feedback from the sensing device. Poor brushers might tire quickly or be unable to withstand the maximum exertion required of them at the start of the instructional program and give up using the device altogether.

SUMMARY OF THE INVENTION

The present invention is designed to operate effectively with any typical toothbrush having an elongated stem and a group of bristles attached to a portion of the stem.

A device in accordance with the present invention includes a mechanism for holding a toothbrush to allow the manual application of force such that, during toothbrushing, the toothbrush pivots about a pivot point. A mechanism adjustably presets the amount of force which is required to be applied to the toothbrush to cause the pivoting motion. A sensing mechanism senses the pivoting motion when the preset amount of force is applied and an indicator is activated.

In a preferred embodiment, the toothbrush holding device of the present invention comprises a toothbrush stem holder having a first cavity at its first end which is adapted to receive a length of the stem. A second cavity is located at a second end of the holder. A fixed, cylindrical electrical contact is carried within and extends from the second cavity. The holder also includes a circumferential O-ring separating ridge and a mechanism for securing the toothbrush stem in the first cavity. A pair of O-rings fit snugly around the outside diameter of the holder, one O-ring being located adjacent either side of the O-ring separating ridge. A sleeve has an inside diameter larger than the outside diameter of the holder to receive the second end of the holder up to and including the circumferential ridge. The sleeve defines a first chamber at a first end and a second chamber at a second end. The first chamber has an O-ring seat, and the second chamber carries an electrical power source. A first electrical contact of an indicator is in electrical contact with a first output terminal of the power source and a fixed plate contact is in electrical contact with a second output terminal of the power source. The first chamber is in communication with the second chamber by means of a connecting chamber. A fixed peripheral, annular contact extends inwardly from the second chamber's peripheral wall and is located next to a side wall of the connecting chamber. The annular contact is in electrical contact with a second electrical contact of the indicator. The annular contact defines an aperture through which the fixed, cylindrical contact extends. When no force is applied to the stem of the toothbrush, the cylindrical contact is located centrally in the aperture defined by the annular contact and, thus, out of contact with it. When the holder is pivoted a sufficient degree about the O-rings and peripheral ridge in the first chamber, the cylindrical contact comes into contact with the annular contact, completing an electrical circuit between the power source and the indicator, thereby activating the indicator, preferably a light bulb. An adjustment cap is threadedly mounted on the first end of the sleeve. The adjustment cap sandwiches the O-rings and the peripheral ridge between itself and the O-ring seat, so that the force required to pivot the holder about the O-rings and ridge can be varied.

BRIEF DESCRIPTION OF THE DRAWINGS

FIG. 1 is a perspective view of a toothbrush holding device in accordance with the present invention.

FIG. 2 is a cross-sectional view taken generally along line 2—2 of FIG. 1.

FIG. 3 is an enlarged sectional view of the electrical contact structure between the toothbrush holder and the electrical power source.

DETAILED DESCRIPTION OF THE INVENTION

As seen in FIG. 1, a toothbrush holding device is indicated generally at 10. Device 10 includes a toothbrush holder 100, pivotally mounted inside a sleeve 200. A conventional toothbrush 12, which has a stem 16 and a group of bristles 14 at one end of stem 16, is removably held within toothbrush holder 100. Holder 100 defines a first cavity 102, which extends longitudinally inward from a first end 103 of the holder, and a second cavity 104, which extends longitudinally inward from a second end 111 of holder 100. A wall 121 separates cavity 102 from cavity 104 and prevents liquid from entering sleeve 200 through the interior of holder 100. Second end 111 includes a reduced diameter portion. Sleeve 200 defines a first chamber 202 at a first end 219, a second chamber 204 at a second end 222, and a connecting chamber 203 between chambers 202 and 204.

Referring now to the FIGS. 1–3 in more detail, toothbrush stem 16 is held within a first cavity 102 of toothbrush holder 100 by securing bolt 106, which passes through a threaded aperture 105 in holder 100. Bolt 106 can be any conventional bolt, preferably with a knurled head which can be readily manipulated by the fingers of a user. Aperture 105 is located adjacent to first end 103 of holder 100, and thus a distance away from first end 219 of sleeve 200, to prevent bolt 106 from interferring with the operation of device 10. A circumferential O-ring separating ridge 108 extends from the outer periphery of holder 100 approximately a third of the length of holder 100 away from first end 103 and defines, at least in part, a fulcrum or pivot area about which holder 100 can pivot with respect to sleeve 200.

Second cavity 104 of holder 100 has fixed within it a fixed contact 110, which is metallic and preferably cylindrical in shape. Preferably, contact 110 is press fit into cavity fixed 104.

Holder 100 is located in first chamber 202 of sleeve 200, and an electrical power source, preferably a battery 206, is located in second chamber 204. The use of battery 206, instead of an external power source, allows device 10 to be totally self-contained, thus reducing the possibility of a dangerous electrical shock to the user. This elimination of external power sources also improves the convenience of the device, because it can be used everywhere. In addition, the device, without an electrical cord, is easier to manipulate during brushing.

Battery 206 provides power to an electrical circuit to selectively energize a light bulb 216. The electrical circuit includes battery 206, annular contact 208, contact plate 212, cylindrical contact 110, bulb contact 215 and light bulb 216.

A cap 224 is threadedly mounted to sleeve 200 at its second end 222. Cap 224 has a central aperture through which bulb 216 extends, fixing it to sleeve 200. An audio device such as a buzzer could be substituted as an indicator for bulb 216; however, the use of a light bulb is preferred.

A ring-shaped support collar 223 is located adjacent to one side of an internal circumferential ridge 225 in connecting chamber 203. Collar 223 is made of an electrically insulating material, and functions as a separator between and support for annular contact 208 and connecting plate 212. Annular contact 208 rests against the side of collar 223 which is furthest from the negative end 227 of battery 206. Contact 212 is fitted within a depression or seat 229 in the side of collar 223 which faces battery 206, and is held therein by a spring 214. Spring 214 is electrically conductive to create an electrical flow path from negative end 227 of battery 206 through spring 214, contact plate 212 and cylindrical contact 110.

Leads 213 are connected to annular contact 208 and extend longitudinally along the exterior of battery 206 and are connected at their opposite end to bulb contact 215. In turn, bulb contact 215 is in electrical contact with the peripheral electrical contact of light bulb 216. The other central electrical contact of light bulb 216 is in contact with the positive end 231 of battery 206. In the position shown in FIGS. 2 and 3, light bulb 216 is not activated because an open circuit exists between cylindrical contact 110 and annular contact 208. However, when cylindrical contact 110 is placed in physical contact with annular contact 208, a closed circuit is established and bulb 216 lights up. This physical contact is accomplished by pivoting holder 102 about a fulcrum area created by ridge 108 and an O-ring 122 when sufficient pressure is applied to bristles 14 during brushing. As will be explained below, the amount of pressure necessary to cause the pivoting can be adjusted.

Elastic O-rings 120, 122 are placed on either side of O-ring separating ridge 108. Ridge 108 and inner O-ring 122 rest in a pivot groove 218 located adjacent to first end 219 of sleeve 200. A restricting cap 220 is threadedly mounted on sleeve 200 at first end 219. Cap 220 includes force gradations 235, the function of which will be discussed below. Cap 220 also includes a central aperture 221 through which holder 100 extends. Cap 220 engages outer O-ring 120, thereby compressing O-rings 120, 122 against ridge 108 to maintain holder 100 in a level, neutral plane within chamber 202. O-rings 120 and 122 also prevent the entry of liquid into the interior of sleeve 200 through its first end. Force exerted on bristles 14, such as would occur when device 10 is moved in a brushing motion against teeth, tends to pivot holder 100, and toothbrush 12 within cavity 202. If sufficient pivoting occurs, because a certain degree of pressure has been applied during brushing, fixed contact 110 will abut fixed contact 212, thereby energizing light 216. Cap 220 can be threadedly tightened further down on sleeve 200 to further compress elastic O-rings 120 and 122 in order to increase the amount of pressure required to pivot holder 100 a sufficient amount to activate light bulb 216. As a result, the amount of O-ring stiffness and resistance to the pivoting of holder 100 inside chamber 202 can be varied. Force gradations 235 on the cap indicate to the user the amount of brushing force required to activate light bulb 216. Preferably, the markings should be in increments of two ounces and range from two to sixteen ounces.

It should be noted that the overall design and configuration of device 10 prevents water and solids from entering the internal chamber of sleeve 200. More particularly, wall 121 prevents access of liquid into the interior of sleeve 200 by way of the interior cavities of holder 100; and O-rings 120, 122 and caps 220, 224 prevent entry of liquid through the opposite ends of sleeve 200. Thus, the design isolates the metallic electrical connections inside sleeve 200.

In operation, the user initially threads cap 220 down upon O-rings 120, 122 so that a brushing force of 2 ounces will light bulb 216. The user is encouraged to tighten the cap weekly to increase the pivoting force necessary to light bulb 216. A two ounce increase is recommended. In this manner, the user is taught to exert increasing amounts of force when brushing, until a full pound of force is realized. This progressive, weekly increase of force permits users to reshape their brushing habits and allows them to achieve in a slow, painless, thorough manner the proper toothbrushing force required for good oral hygiene.

Of course, it should be understood that changes can be made to the disclosed preferred embodiment. Thus, it will be obvious to one of ordinary skill in the art that numerous modifications may be made without departing from the true spirit and scope of the invention, which is to be limited only by the appended claims.

We claim:

1. A device for indicating that a force being applied by a toothbrush against teeth exceeds a variable, preset value, comprising:
   holding means for holding a toothbrush to allow manual application of force to the toothbrush during toothbrushing to cause pivoting motion of the toothbrush about a pivot point;
   adjustment means for adjustably presetting the amount of force required to be applied to the toothbrush to cause said pivoting motion;
   sensing means for sensing said pivoting motion when said preset amount of force is applied to said toothbrush; and
   indicator means for indicating when said sensing means senses said pivoting motion.

2. A device in accordance with claim 1 wherein said holding means includes a holder adapted to removably hold the toothbrush, a sleeve into which said holder extends and a means for defining a pivot area about which said holder can pivot with respect to said sleeve.

3. A device in accordance with claim 2 wherein said means defining a pivot area includes a ridge located about the outer periphery of said holder.

4. A device in accordance with claim 3 wherein said adjustment means includes means for adjustably applying pressure to said ridge.

5. A device in accordance with claim 2 wherein said adjustment means includes at least one O-ring located about the outer periphery of said holder and means for adjustably applying pressure between said at least one O-ring and said holder.

6. A device in accordance with claim 1 wherein said sensing means includes a fixed contact and a movable contact of an electrical circuit, said movable contact being connected to said holder, and said indicator means including an electrically actuated indicator device in said electrical circuit.

7. A device in accordance with claim 1 including means for displaying the amount of force required to activate said indicator means.

8. A device for indicating that a predetermined force is being applied against teeth by a toothbrush having an elongated stem and a group of bristles attached to a portion of the stem, comprising:
   a toothbrush holder having a cavity at a first end adapted to receive a length of the toothbrush stem and anopposite second end, and means for securing the stem in said cavity;
   a sleeve having a hollow interior into which the second end of said holder is received;
   pivot means mounted to the exterior of said holder, said pivot means acting as a fulcrum about which said holder pivots inside of said sleeve;
   adjustable resistance means for variably resisting the pivoting of said holder inside said sleeve;
   sensing means located in said sleeve for sensing the pivoting of said holder in said sleeve; and
   indicating means for indicating when said sensing means senses the pivoting of said holder.

9. A device in accordance with claim 8 wherein said adjustable resistance means includes means for adjustably applying pressure to said pivot means.

10. A device in accordance with claim 9 wherein said pivot means includes a ridge extending from the exterior periphery of said holder.

11. A device in accordance with claim 10 wherein said pressure applying means includes a pair of compressible O-rings disposed about said ridge and an adjustable cap carried by said sleeve, said cap being adjustably positionable on said sleeve to adjustably apply a compressive force to said O-rings.

12. A device in accordance with claim 11 including gradations on said cap to indicate the amount of force required to activate said indicator means.

13. A device in accordance with claim 8 wherein said sensing means includes a fixed electrical contact extending from the second end of said holder and an annular shaped electrical contact having a central aperture into which said floating contact extends, said aperture being sized such that said fixed contact is not in contact with the edge of the aperture when the holder is in a nonpivoted position.

14. A device in accordance with claim 13 wherein said indicating means includes an electrical circuit with an electrically activated indicator and said fixed and annular contacts, said indicator being deactivated when said holder is in a nonpivoted position and activated when said holder is pivoted and said fixed contact is placed in contact with the edge of the aperture in said annular contact.

15. A device for indicating that a predetermined force is being applied against teeth by a toothbrush having an elongated stem and a group of bristles attached to a portion of the stem comprising:
   a toothbrush holder having a first cavity at a first end and a second cavity at a second opposite end, a dividing wall separating said first cavity from said second cavity to prevent the passage of liquid from said first cavity to said second cavity, said first cavity being adapted to receive a length of the toothbrush stem, said holder having a generally cylindrical outer surface;
   a fixed electrical contact being fixed by and extending from said second cavity;
   a peripheral ridge extending from the outer periphery of said holder;
   means for securing the stem of the toothbrush in said first cavity;
   a pair of O-rings adapted to fit snugly around the outside diameter of said holder, one O-ring being located adjacent either side of said peripheral ridge;
   a sleeve having a generally cylindrical shaped hollow interior defining a first chamber at a first end thereof with an inside diameter larger than the outside diameter of said holder and a second chamber at an opposite second end adapted to hold a battery, said second end of said holder up to and including said circumferential ridge being received in said first chamber of said sleeve, said first chamber having an O-ring seat adjacent to said first end for receiving at least one of said O-rings and at least a portion of said ridge;
   an electrical circuit located in said second chamber for connection to a battery to be placed in said second chamber;
   an electrical indicator electrically connected to said electrical circuit for activation when said circuit is closed;
   said electrical circuit including a fixed contact, an annular contact, a contact plate, and first and second terminals of said indicator, the first terminal of said indicator being adapted to be in contact with a first terminal of the battery, the second terminal being in electrical contact with said annular contact, said contact plate being adapted to be in electrical contact with a second terminal of the battery, said fixed contact extending through an aperture in said annular contact and touching said contact plate, in a nonpivoted position of said holder said fixed contact being out of physical contact with the edge of said aperture in said annular contact to open said circuit, and in a sufficiently pivoted position said fixed contact contacts the edge of said aperture in said annular contact to close said circuit and activate said indicator; and an adjustment cap threadedly mounted on said first end of said sleeve, said adjustment cap sandwiching said O-rings and said peripheral ridge between said adjustment cap and said O-ring seat to apply a compressive force on the O-rings, so that the force required to pivot said holder about said O-rings and said ridge can be varied by adjusting the position of said cap on said sleeve to adjust the force applied by said cap on said O-rings.

16. A device in accordance with claim 15 wherein the second end of said holder tapers to a smaller outer diameter.

17. A device in accordance with claim 15 wherein said indicator comprises a light bulb.

18. A device in accordance with claim 17 wherein said light bulb is mounted on said sleeve by means of a retaining cap threadedly mounted on the second end of said sleeve, said retaining cap having a central aperture through which said bulb extends.

19. A device in accordance with claim 15 wherein a nonconductive annular collar separates said annular contact from said contact plate.

20. A device in accordance with claim 19 wherein said floating contact is spring biased into engagement with said contact plate.

* * * * *